United States Patent
Evitt et al.

(10) Patent No.: US 12,030,849 B2
(45) Date of Patent: Jul. 9, 2024

(54) LIQUID ISOMERIZATION FOR METHATHESIS PROCESS

(71) Applicant: Technip Process Technology, Inc., Houston, TX (US)

(72) Inventors: Steven Evitt, Houston, TX (US); Cornelis F. Van Egmond, Houston, TX (US); Veronique Reich, Le Trait (FR); Yvon Simon, Le Trait (FR); Bruno Destour, Le Trait (FR)

(73) Assignee: TECHNIP PROCESS TECHNOLOGY, INC., Houston, TX (US)

( * ) Notice: Subject to any disclaimer, the term of this patent is extended or adjusted under 35 U.S.C. 154(b) by 0 days.

(21) Appl. No.: 16/613,790

(22) PCT Filed: Feb. 13, 2018

(86) PCT No.: PCT/US2018/017957
§ 371 (c)(1),
(2) Date: Nov. 14, 2019

(87) PCT Pub. No.: WO2018/212812
PCT Pub. Date: Nov. 22, 2018

(65) Prior Publication Data
US 2020/0071245 A1 Mar. 5, 2020

Related U.S. Application Data

(60) Provisional application No. 62/506,047, filed on May 15, 2017.

(51) Int. Cl.
*C07C 6/04* (2006.01)
*C07C 5/25* (2006.01)
(Continued)

(52) U.S. Cl.
CPC .......... *C07C 6/04* (2013.01); *C07C 7/04* (2013.01); *C07C 5/25* (2013.01); *C07C 11/06* (2013.01); *C07C 11/08* (2013.01)

(58) Field of Classification Search
CPC .... C07C 6/04; C07C 6/00; C07C 6/02; C07C 7/04; C07C 5/25
See application file for complete search history.

(56) References Cited

U.S. PATENT DOCUMENTS 5,898,091 A 4/1999 Chodorge et al.
6,166,279 A * 12/2000 Schwab ................ B01D 3/141
585/312

(Continued)

FOREIGN PATENT DOCUMENTS

EP 0742195 A1 11/1996
EP 1110934 A1 6/2001
(Continued)

OTHER PUBLICATIONS

International Search Report and Written Opinion issued in corresponding PCT application No. PCT/US2018/17957 dated Apr. 9, 2018.

(Continued)

*Primary Examiner* — Youngsul Jeong
(74) *Attorney, Agent, or Firm* — Locke Lord LLP; Gabrielle L. Gelozin; Christopher J. Capelli

(57) ABSTRACT

The present disclosure relates to processes for improved yields of propylene via metathesis, primarily from the conversion of $C_4$ and $C_5^+$ olefins obtained from steam or fluid catalytic cracking of hydrocarbons. In particular, the present disclosure relates to processes for preparing propylene by improved isomerization of 1-butene to 2-butene relative to the metathesis reaction.

21 Claims, 5 Drawing Sheets

(51) Int. Cl.
*C07C 7/04* (2006.01)
*C07C 11/06* (2006.01)
*C07C 11/08* (2006.01)

(56) References Cited

U.S. PATENT DOCUMENTS

| | | | |
|---|---|---|---|
| 7,459,593 B1* | 12/2008 | Krupa | C07C 2/08 585/259 |
| 7,576,251 B2 | 8/2009 | Gartside et al. | |
| 2002/0169346 A1 | 11/2002 | Commereuc et al. | |
| 2008/0312481 A1* | 12/2008 | Leyshon | C07C 6/04 585/324 |
| 2010/0041930 A1 | 2/2010 | Gartside et al. | |
| 2010/0286458 A1 | 11/2010 | Iselborn et al. | |
| 2016/0023964 A1 | 1/2016 | Choi et al. | |

FOREIGN PATENT DOCUMENTS

| | | |
|---|---|---|
| EP | 2563749 A1 | 3/2013 |
| FR | 2802920 A1 | 6/2001 |
| WO | 2012147047 A1 | 11/2012 |

OTHER PUBLICATIONS

Extended European Search Report issued during prosecution of corresponding European Patent Application No. 18802445.9 on Mar. 24, 2021. (8 pages).

Russian Office Action and English Translation thereof issued during prosecution of the corresponding Russian Patent Application No. 2019139021/04(076745) dated May 27, 2021.

Indian Examination Report issued during prosecution of the corresponding Indian Patent Application No. 201937051227 dated Jun. 7, 2021.

* cited by examiner

LIQUID ISOMERIZATION FOR METHATHESIS PROCESS

CROSS REFERENCE TO RELATED APPLICATIONS

This Application is a U.S. National Stage Entry of International Application no. PCT/US2018/017957, filed on Feb. 13, 2018 which claims the benefit of U.S. Provisional Application No. 62/506,047, filed on May 15, 2017, the entire contents of which are hereby incorporated herein by reference in their entirety.

TECHNICAL FIELD

Embodiments presented herein generally relate to the processing of hydrocarbons from a cracking process, such as steam or fluid catalytic cracking, primarily for conversion of $C_4$ and $C_5^+$ olefins to propylene via metathesis. More specifically, embodiments disclosed herein relate to processes for preparing propylene by improved isomerization of 1-butene to 2-butene relative to the metathesis reaction.

DESCRIPTION OF THE RELATED ART

Propylene (i.e., propene) is one of the fastest growing petrochemicals primarily because of the high growth rate of polypropylene. Typically, about 55% of this propylene is generated by steam cracker, 30% by refinery fluid catalytic cracking (FCC) units, and 15% by on-purpose processes like propane dehydrogenation or metathesis. The growth rate of the propylene demand has outpaced the demand for ethylene growth rate, which is also produced from steam cracker. As a result, the construction of new steam crackers to meet the increasing ethylene demand alone will not be sufficient to satisfy the growing propylene demand. To make up for this shortfall, other propylene supply sources will be required. Therefore, additional emphasis is being given on recovering propylene from steam cracker, FCC, DCC (Deep Catalytic Cracking) units, and the like. As such, market demand for propylene will have to be met by other processes, for example, improved recoveries from steam cracking, FCC, and DCC units.

U.S. Pat. No. 6,166,279 discloses a process for the preparation of olefins from steam cracker or refinery $C_4$ streams. The process requires a first-stage auto-metathesis of a $C_4$ stream essentially free of butadiene and isobutylene that converts 1-butene and 2-butene present in the $C_4$ stream into propene and $C_{5+}$ fraction and a subsequent second-stage metathesis reaction of the 2-pentene and 3-hexene with introduced ethylene to form 1-butene and propylene. 1-butene issued from the second-stage metathesis or 1-butene issued from first-stage metathesis may be isomerized and recirculated to the first-stage metathesis.

U.S. Pat. No. 6,271,430 discloses a two-step process for the production of propylene. The first step consists of reacting 1-butene and 2-butene in a $C_4$ stream essentially free of butadiene and isobutylene in an auto-metathesis reaction to form propylene and 2-pentene. The products are then separated in the second step. The third step reacts specifically the 2-pentene with ethylene to form propylene and 1-butene. The pentenes recycled and reacted with ethylene are normal pentenes (2-pentene).

U.S. Pat. No. 7,459,593 discloses a process for integrating a butene dimerization process with a metathesis process to remove isobutene from the feed stream to the metathesis reactor. The isobutene is dimerized in the dimerization process to leave n-butenes for metathesis with ethylene. A pre-metathesis selective hydrogenation process isomerizes 1-butenes to 2-butenes is also included in the process.

U.S. Pat. No. 7,576,251 discloses a process for the preferentially converting 1-butene and 2-butene for propylene production. The process includes hydroisomerizing the feed stream to convert a portion of the 1-butene to 2-butene and passing the hydro-isomerization effluent through a fractionation column from which a recycle stream rich in 1-butene is withdrawn and sent back to hydroisomerization reactor in order to increase the overall yield of the isomerization step. The bottom of the fractionation column rich in 2-butene is sent to a metathesis reaction to provide a product stream containing propylene, butenes and $C_{5+}$ hydrocarbons.

As described above, there is considerable interest in the processing of $C_4$ olefin streams to produce lighter olefins, such as propylene. In some of the above processes, $C_{4+}$ are further processed to boost propylene production. Accordingly, there exists a significant need for processes that increase the yield of propylene from such olefin-containing streams at low cost and low energy.

SUMMARY OF THE DISCLOSURE

According to an embodiment a method is disclosed for the production of propylene from ethylene and butene comprising: isomerizing under liquid phase conditions a hydrocarbon stream in an isomerization reactor; and providing an isomerized hydrocarbon stream to a metathesis reactor, wherein the isomerization reactor converts a portion of 1-butene to 2-butene and is located before and/or after the metathesis reactor, or in a butene concentrated recycle stream(s).

According to another embodiment a process is disclosed for the production of propylene from ethylene and butene, the process comprising: (i) combining a hydrocarbon stream comprising n-butenes and paraffins in which butadiene is limited to a maximum of about 0.5 weight percent and isobutylene is limited to maximum of about 10 weight percent with an ethylene stream; (ii) contacting the combined hydrocarbon stream and ethylene stream of step (i) in a metathesis reactor with a metathesis catalyst to form a product stream comprising ethylene, propylene, $C_4$ olefins comprising 2-butene and 1-butene, heavier olefins, and paraffins; (iii) separating the ethylene from the product stream to provide a recycle ethylene stream and a bottoms stream comprising propylene, paraffins, $C_4$ olefins comprising 2-butene and 1-butene, and $C_{5+}$ hydrocarbons; (iv) fractionating the bottoms stream to provide at least a propylene fraction, a fraction comprising paraffins, olefins, 2-butene, 1-butene, and $C_5$ hydrocarbons (butene concentrated recycle stream), and a $C_{4+}$ hydrocarbon fraction; (v) recycling the recycle ethylene stream of step (iii) and the butene concentrated recycle stream of step (iv) to step (i), and (vi) isomerizing under liquid phase conditions in a liquid phase isomerization reactor at least one stream selected from the group consisting of the butene concentrated recycle stream prior to step (i) [FIG. 2], the hydrocarbon stream (and optionally the ethylene stream, and/or the ethylene recycle stream) prior to step (i) [FIG. 3], a combination stream comprising the butene concentrated recycle stream and the hydrocarbon stream (and optionally the ethylene stream, and/or the ethylene recycle stream) prior to step (i) [FIG. 4], and the product stream prior to step (iii) [FIG. 5], to provide said propylene.

The inventors have found that isomerization in an external liquid phase isomerization reactor at a temperature below that of the metathesis reactor is particularly effective for increasing propylene production from feedstocks rich in 1-butene.

Additionally, the inventors have found that the use of optimized levels of 2-pentene in the $C_4$ recycle stream prevents 1-butene from consuming 2-butene or propylene in the metathesis reactor via side reactions, which ultimately leaves more 2-butene available for the metathesis reactions of 2-butene plus ethylene to yield propylene, all of which is more fully described below.

Unless specified otherwise, the hydrocarbon feeds as more broadly discussed in the following detailed description of the invention including embodiments of the Figures are defined as: a Raffinate I (Raff I), which is a $C_4$ stream essentially free of butadiene; a Raffinate II (Raff II), which is $C_4$ stream substantially free of butadiene and isobutylene; and a Raffinate III (Raff III) which is a $C_4$ stream essentially free of butadiene, isobutylene and 1-butene.

The following are some reaction schemes of various compounds described herein as they relate to the metathesis and isomerization reactions, respectively.

The metathesis main reactions include:
Ethylene+2-Butene (cis)<-->2 Propylene
Ethylene+2-Butene (trans)<-->2 Propylene
    The metathesis side reactions:
        1-Butene+2-Butene (cis)<-->Propylene+2-Pentene
1-Butene+2-Butene (trans)<-->Propylene+2-Pentene
1-Butene+Propylene<--> Ethylene+2-Pentene
1-Butene+1-Butene<-->Ethylene+Hexene
    Isomerization of 2-butene:
2-Butene (cis)<-->2-Butene (trans)
    2-butenes and 1-butene isomerization:
1-Butene<-->2-Butene (cis)
1-Butene<-->2-Butene (trans)

DETAILED DESCRIPTION OF THE INVENTION

Figure 1:
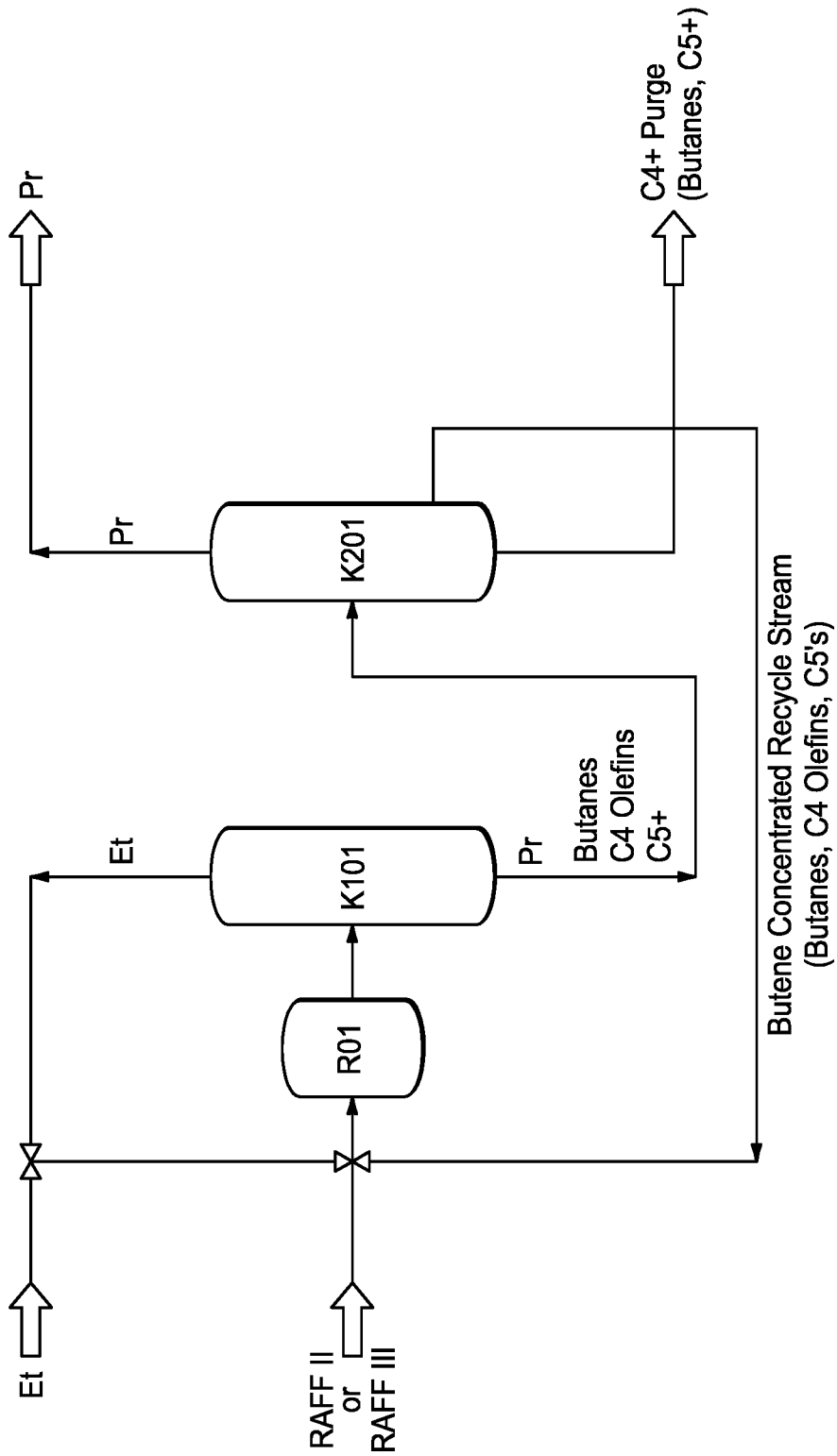
FIG. 1 is a schematic process flow diagram of a conventional metathesis scheme. The process is a metathesis of a $C_4$ stream with introduced ethylene to form propylene.

Thermal cracking and catalytic cracking can create a variety of products. Feedstock of these units ranges from ethane to vacuum gas oil. Various products may be produced from such systems, including a gasoline product and/or a light product such as propene and/or ethene.

For example, in typical olefin plants there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture may be separated into different carbon numbers, typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut, consisting of $C_4$ acetylenes, butadiene, iso- and normal butenes, and iso- and normal butane can be processed in many ways. A typical steam cracker $C_4$ cut (for intermediate cracking severity, i.e. P/E=0.61) contains $C_4$ acetylenes in trace amounts; approximately 45 mol percent butadiene; approximately 19 mol percent 1-butene; approximately 10 mol percent 2-butene; approximately 20 mol percent isobutylene; and approximately 6 mol percent iso- and normal butanes.

The components in a refinery or FCC based $C_4$ cut are similar, with the exception that the percentage of paraffins are considerably greater.

Typically, butadiene and $C_4$ acetylenes are removed first. This can be accomplished by either hydrogenation or extraction. The product from butadiene and $C_4$ acetylene removal is designated Raffinate I. If extraction is employed, the remaining 1-butene and 2-butene remain essentially in the same ratio as that of the initial feedstock. If hydrogenation is employed, the initial product from butadiene hydrogenation is 1-butene. However hydro-isomerization catalyst oriented towards 2-butene can be used within the same reaction system changing the 1-butene to 2-butene. The extent of this reaction depends upon catalyst and reaction conditions (temperature and hydrogen excess) within the hydrogenation system. It is common practice to limit the extent of hydrogenation in order to avoid excess production of butanes from butenes and thus prevent loss of butene feedstock for downstream operations. The butenes remaining in the mixture consist of normal olefins (1-butene, 2-butene) and iso-olefins (isobutylene). The balance of the mixture consists of both iso- and normal-butanes from the original feed plus what was produced in the hydrogenation steps and any small quantity of unconverted or unrecovered butadiene.

A Raffinate I stream can be further processed in many ways. A Raffinate II stream is by definition a stream following isobutylene removal. Isobutylene can be removed, for example, by fractionation. However, with fractionation isobutane is removed along with the isobutylene, as well some fraction of the 1-butene. The resultant Raffinate II will contain primarily normal olefins and paraffins and minimal iso-olefins and iso-paraffins.

Isobutylene can also be removed by various reactions which include: reaction with methanol to form MTBE, reaction with water to form tertiary butyl alcohol, or reaction with itself to form a $C_8$ gasoline component. In all reaction cases, the paraffins are not removed, and the effluent contains both normal and iso-paraffins. The paraffin content and composition of the Raffinate II impacts downstream processing options.

A Raffinate III stream would be the $C_4$ cut less the butadienes, isobutylene, and 1-butene. 1-butene is generally removed by fractionation. The resultant Raffinate III will contain primarily normal paraffin, 2-butene and minimal 1-butene, iso-butene and iso-paraffins.

The butenes have many uses and one important use is for the production of propylene via metathesis. The butenes are also used for the production of ethylene and hexene via metathesis. Conventional metathesis involves the reaction of 1-butene and 2-butene with ethylene (principally the reaction of 2-butene with ethylene) to form propylene, and the reaction of 1-butene with 2-butene to form propylene and pentene (side reaction). These reactions occur in the presence of a group VIA or VIIA metal oxide catalyst, either supported or unsupported. The paraffin components of the reaction feed are essentially inert and do not react, and are typically removed from the process via a purge stream in the separation system that follows the metathesis reactor. Typical catalysts for metathesis are tungsten oxide supported on silica or rhenium oxide supported on alumina.

The reaction of isobutylene with ethylene is non-productive and reaction with itself and/or other $C_{4s}$ is limited in the presence of excess ethylene. Thus, isobutylene (isobutene) is usually removed from the feedstock prior to the metathesis reaction step. Non-productive reactions essentially occupy catalyst sites but produce no product. If allowed to remain in the feed to the metathesis unit, the concentration of this non-reactive species would build up creating capacity limitations.

The reaction of 1-butene with ethylene is also non-productive. However, it is conventional to employ a double bond isomerization catalyst within the metathesis reactor to shift 1-butene to 2-butene and allow for continued reaction. Typical double bond isomerization catalysts include basic metal oxides (Group IIA), either supported or unsupported. Magnesium oxide and calcium oxide are examples of such double bond isomerization catalysts that may be physically admixed with the metathesis catalyst. No equivalent co-catalyst exists for the skeletal isomerization of isobutylene to normal butene.

Typically metathesis processes utilize Raffinate II. The Raffinate II is then admixed with ethylene, passed through guard beds to remove poisons, vaporized and preheated and fed to the metathesis reactors. The operating conditions are typically 300° C. and 20 to 35 bar pressure. The reactor effluent following heat recovery is then separated in a fractionation system. First the ethylene is recovered overhead in a first tower and recycled to the reactor system. The tower bottoms are then sent to a second tower where the propylene is recovered overhead. A side draw is taken containing the majority of the unconverted $C_4$ components and recycled to the reactor. The tower bottoms containing the $C_5$ and heavier products plus some $C_4$ olefins and $C_4$ paraffins are sent to purge. The purge rate is typically fixed to contain sufficient $C_4$ paraffins to avoid their buildup in the reactor recycle stream. In some cases, a third tower is employed on the tower bottoms stream to separate the $C_4$ components overhead and the $C_5$ and heavier components as a bottom stream.

It is well known that metathesis catalysts and the double bond isomerization catalysts are quite sensitive to poisons. Poisons include water, $CO_2$, oxygenates (such as MTBE), sulfur compounds, nitrogen compounds, and heavy metals. It is common practice to employ guard beds upstream of the metathesis reaction system to insure the removal of these poisons. It does not matter if these guard beds are directly before the metathesis reaction system or further upstream as long as the poisons are removed and no new poisons are subsequently introduced.

Metathesis reactions are very sensitive to the location of the olefin double bond and the stereo-structure of the individual molecules. During the reaction, the double bond on each pair of olefins adsorb on the surface and exchange double bond positions with the carbon groups on either sides of the double bonds. Metathesis reactions can be classified as productive, half productive or non-productive. Non-productive reactions result in essentially no reaction taking place. When the double bonds shift with metathesis reaction, the new molecules are the same as the originally adsorbed molecules, thus no productive reaction occurs. This is typical for reactions between symmetric olefins or reactions between ethylene and alpha olefins. If fully productive reactions occur, new products are generated no matter which orientation the molecules occupy the sites. The reaction between ethylene and 2-butene to form two propylene molecules is a fully productive reaction. Half productive reactions are sterically inhibited. If the pair of olefins adsorb in one orientation (typically the cis position with respect to the attached R groups), when the double bonds shift, new products are formed. Alternately if they adsorb in a different steric configuration (the trans position), when the bonds shift, the identical olefins are formed and thus no new products are formed. The various metathesis reactions proceed at different rates, for example, a fully productive reaction is usually faster than a half productive reaction.

Conventional metathesis is defined as the reaction of the $C_4$ olefin stream with ethylene. However, the $C_4$ stream can also react in the absence of ethylene as a feedstock. This reaction is called auto or self metathesis. Examples of the auto or self metathesis would be the reaction of 1-butene and 2-butene to produce propylene and 2-pentene; 1-butene+1-butene to produce ethylene+hexene-3; isobutylene+2-butene to produce propylene+2-methyl 2-butene; and isobutylene+1-butene to produce ethylene+2-methyl 2-pentene.

In conventional metathesis, the focus is to maximize the reaction of 2-butene+ethylene to produce 2 propylene. As such, excess ethylene is used to reduce the extent of the reactions of butenes with themselves, i.e., the reactions described supra. The theoretical ratio is 1/1 molar or 0.5 weight ratio of ethylene to n-butenes, but it is common in conventional metathesis to employ significantly greater ratios, typically, 2 or larger molar ratio to minimize said reactions of butenes with themselves.

Typically it is desirable to increase the 2-butene content of the metathesis reactor feed by subjecting butylene to isomerization to convert 1-butene to additional 2-butene. Conventional propylene production systems place the isomerization reactor having vapor phase conditions in a place that favors lower piece count but does not favor the 2-butene to 1-butene equilibrium, as more fully described below. The isomerization is then often performed in a dedicated reaction zone of the olefin metathesis reactor under vapor phase (isomerization and metathesis having same operating conditions).

However, the inventors have found that propylene's ultimate yield can be improved and the equipment to obtain the improved yields can be reduced in size by utilizing liquid phase isomerization conditions in an isomerization reactor that is located before, e.g., the fresh feed stream, and/or after the metathesis reactor, or in any butene concentrated recycle streams. The processes described herein improve the ratio of 2-butene in the metathesis reaction with ethylene that yields 2 molecules propylene, thus maximizing propylene yield.

Importantly, the equilibrium reaction of 1-butene to 2-butene is favored by lower temperatures. According to an embodiment herein, an external isomerization reactor operating under liquid phase isomerization condition provides maximum propylene production. The external isomerization reactor operating under liquid phase conditions ensures higher conversion of 1-butene- to 2-butene and thus provides better selectivity, conversion, and ultimate yield of the overall metathesis process. Typical liquid phase isomerization conditions of the processes herein include a temperature range of about 40° C.-100° C. and a typical pressure range of 20-35 barg in presence of small amount of hydrogen The processes disclosed herein improve the ultimate propylene yield for the metathesis process through optimization of the location the isomerization step and utilization of the lower temperature conditions associated with the liquid phase isomerization which favors the equilibrium reaction of 1-butene to 2-butene compared to vapor phase conditions of isomerization and metathesis reactions. Reducing the amount of 1-butene at the inlet of metathesis reactor increases the selectivity of metathesis towards the production of propylene by reducing the amount of side reactions.

The processes disclosed herein for improved yields of propylene include placing a liquid phase isomerization reaction before or after a metathesis reaction and/or within a $C_4$ feedstock (i.e., fresh feed stream) issued from steam cracking and/or from Refinery FCC, and/or $C_4$ raffinate (from butadiene extraction, from MTBE/ETBE/iso-octene units, and the like) and/or within a butene concentrated recycle stream with or without $C_5$ hydrocarbons so that the concentration of 1-butene to the isomerization reaction is increased. The 1-butene to 2-butene isomerization reaction is equilibrium limited by 2-butene concentration, thus, by increasing the consumption of 2-butene in the metathesis reaction the isomerization provides greater conversion of 1-butene to 2-butene. Importantly, the equilibrium reaction of 1-butene to 2-butene is favored by lower temperatures existing post metathesis.

The relationship of the aforementioned equilibrium between 1-butene and 2-butene and how it relates to temperature is supported by the experimental data disclosed below.

The Figures and Examples as more fully described below present the improved propylene processes, which increase piece count due to the addition of one external isomerization reactor, however, reduces energy by at least about 10%, as well as, reducing the overall size of equipment by at least about 15%. The inventors base these estimates on the reduction in butene concentrated recycle stream versus the commercial version of metathesis reaction The processes disclosed herein for improved yields of propylene by placing a liquid phase isomerization reactor before or after a metathesis reactor also present the advantage to increase metathesis catalyst life time compared to conventional metathesis process that combine isomerization and metathesis catalyst in the same reactor. Indeed isomerization catalyst and metathesis catalyst does not have same deactivation rate (i.e., they not have same optimized cycle time). Having two different reactors allow optimizing both cycle length and regeneration conditions of each catalyst. Isomerization catalyst is known to require frequent regeneration whereas metathesis catalyst is less sensitive to deactivation. On the other hand metathesis catalyst is less robust to the high temperature required during regeneration compared to isomerization catalyst. Thus by limiting number of oxi-regeneration of metathesis catalyst compared to isomerization catalyst, catalyst life time is optimized.

The embodiments of processes presented herein provide for increase the amount of 1-butene to the liquid phase isomerization reactor for conversion to 2-butene and to convert the 2-butene from the liquid phase isomerization reactor with ethylene in the metathesis reactor to produce propylene. The embodiments of the disclosed processes are more fully explained below.

The processes of the invention are illustrated in the Figures, which are intended only to describe certain embodiments of the invention and are not intended to limit either their application or scope.

In the Figures the feeds used in the processes for producing propylene are from the steam cracking of heavy hydrocarbon molecules, such as naphtha. Steam cracking of such heavy hydrocarbons produces smaller unsaturated molecules along with some methane and hydrogen. The most prevalent molecule produced from steam cracking is ethylene. In the $C_4$ cut of the steam cracker product there is 1-butene, 2-butenes, isobutylene, butadienes and some butanes. Raffinate-2 and Raffinate-3 streams, as defined previously, are designations of processing this $C_4$ cut.

FIG. 1 is a schematic process flow diagram of a conventional metathesis scheme. The process is a metathesis of a $C_4$ stream, i.e., a Raff II or Raff III, with metathesis reactor (R01) and introduces ethylene (Et) to form propylene (Pr). R01 is operated under vapor phase at typical temperature of 300-400° C. In order to boost propylene production, R01 can also have a functionality to isomerize part of 1-butene to 2-butene (including a dedicated layer dedicated to isomerization located upstream the metathesis catalyst). Reactor effluent from R01 is further processed in a deethylenizer K-101 to provide propylene, butanes, $C_4$ olefins, and $C_{5+}$ to depropylenizer K-201. Recovered ethylene from K-101 is recycled back to R01. A side-draw from depropylenizer K-201, i.e., a butene concentrated stream containing some $C_4$ paraffins, most of $C_4$ olefins, and some $C_5$ is also recycled to R01. K-201 bottoms ensure purging of $C_4$ paraffins that would otherwise buildup in the reactor recycle stream. Purge also contains un-recycled $C_4$ olefins, un-recycled $C_5$ and heavier products.

The process of FIG. 1 can favor the following reactions in the metathesis reactor: ethylene plus (cis) 2-butene<--->2 propylene; and ethylene plus (trans) 2-butene<--->2 propylene.

Figure 2:
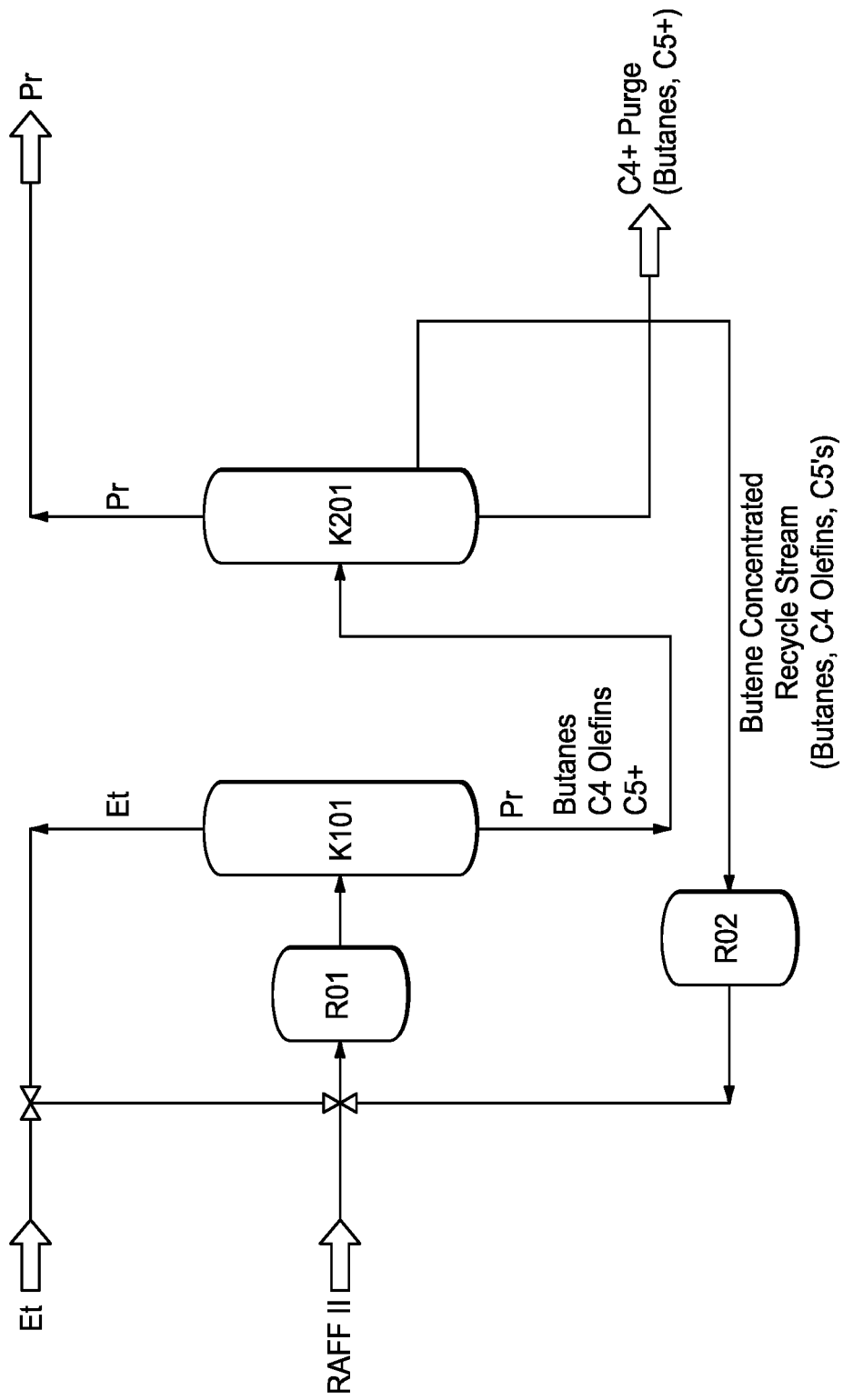
FIG. 2 is a schematic process flow diagram of a first embodiment in which a propylene product is produced utilizing a liquid isomerization reaction of a butene concentrated recycle stream prior to the butene concentrated recycle stream being mixed with an ethylene feed stream and a Raff II feed stream (i.e., fresh feed stream) and entering a metathesis reactor. The pentene content of the butene concentrated stream is optimized to block 1-butene side reactions in the metathesis reactor.

FIG. 2 presents an embodiment utilizing an external liquid phase isomerization reactor (R02) in the butene concentrated recycle stream prior to the metathesis reactor (R01). The R01 is operated under vapor phase at typical temperature of 300-400° C. The R02 reactor is operated under liquid phase conditions, at a lower temperature range of about 40° C.–100° C. and at typical pressure range of 20-35 barg in presence of small amount of hydrogen. R02 catalyst is typically a palladium based catalyst. The reaction of 1-butene to 2-butene, which is equilibrium dependent, being favored by lower temperatures than the one required for metathesis, the lower temperature of the external liquid phase isomerization reactor (R02) advantageously maximizes the reaction of 1-butene to 2-butene and thereby increases the amount of 2-butene in the recycle stream. In addition to this advantageous temperature effect, by first consuming the 2-butene via the metathesis reaction with ethylene, the 1-butene concentration to the external isomerization reactor in the recycle is increased and 2-butene concentration is reduced compared to conventional scheme using a single vapor phase reactor (having a dedicated layer for isomerization located upstream the metathesis catalyst). This brings positive impact for the external isomerization reactor, since the isomerization of 1-butene to 2-butene is limited by equilibrium, the conversion of total 1-butene to 2-butene is improved by reducing the concentration ratio of 2-butene to 1-butene in the feed.

Metathesis reactor R01 processes a Raff II stream combined with the isomerized butene concentrated recycle stream and an ethylene stream, and provides a product stream comprising ethylene, propylene, $C_4$ olefins comprising 2-butene and 1-butene, heavier olefins, and paraffins. The external isomerization step ensuring a higher 2-butene content at inlet of the metathesis reactor thus provides better selectivity, conversion, and ultimate yield of the overall metathesis process. The product stream from R01 is processed in a deethylenizer K-101 to separate ethylene and a bottoms stream comprising propylene, butanes ($C_4$ paraffins), $C_4$ olefins, and $C_{5+}$ that is forwarded to depropylenizer K-201. The recovered ethylene from K-101 deethylenizer is recycled back to the R01 metathesis reactor. Depropylenizer K-201 separates propylene and a butene concentrated recycle stream side stream which is sent back to R-01 and a bottom cut. The butene concentrated recycle stream from depropylenizer K-201 contains some $C_4$ paraffins, most of $C_4$ olefins, and some $C_5$.

The bottom cut of the depropylenizer K-201 ensures purging of $C_4$ paraffins that would otherwise buildup in the reactor recycle stream. It is thus rich in butanes but also contains butenes that are not easily separated from butanes, un-recycled $C_5$ and heavier products. $C_{5+}$ content in the bottom cut is most of the time less than 20% if Raff II fresh feed is a $C_4$ cut with low $C_5$ content.

The pentene content of the butene concentrated recycle stream is optimized to block 1-butene side reactions in the metathesis reactor. 2-pentene compounds, although not desired for metathesis to propylene, are used to limit the 1-butene reactions in the metathesis reactor (R01). It is important to note that all the reactions, for both isomerization reactions and metathesis reactions, of the processes disclosed herein are equilibrium limited. It is desirable to promote the metathesis reaction of ethylene and 2-butene because it produces 2 moles of propylene. However, undesirable metathesis reactions, i.e., less efficient reactions that make propylene, such as, 1-butene plus 2-butene which produces 1 mole of propylene and 1 mole of 2-pentene, or reaction that are consuming propylene, such as, 1-butene plus propylene which produces 1 mole of 2-pentene and 1 mole of ethylene can be reduced by supplying sufficient amounts of 2-pentene to shift equilibrium on these undesirable metathesis reactions towards butene side, thereby increasing the amount of 2-butene available to react with propylene. Since reactions in concern are equilibrium dependent, required pentene content of the butene concentrated recycle stream to block 1-butene side reactions in the metathesis reactor is highly dependent of the quantity of other components in concern, especially 1-butene versus 2-butene in the metathesis reactor. Pentene content in the butene concentrated recycled is thus optimized case by case depending of the fresh feed composition by means of process control of depropylenizer K-201 such as reflux flow, reboiling rate and side-draw location.

Figure 3:
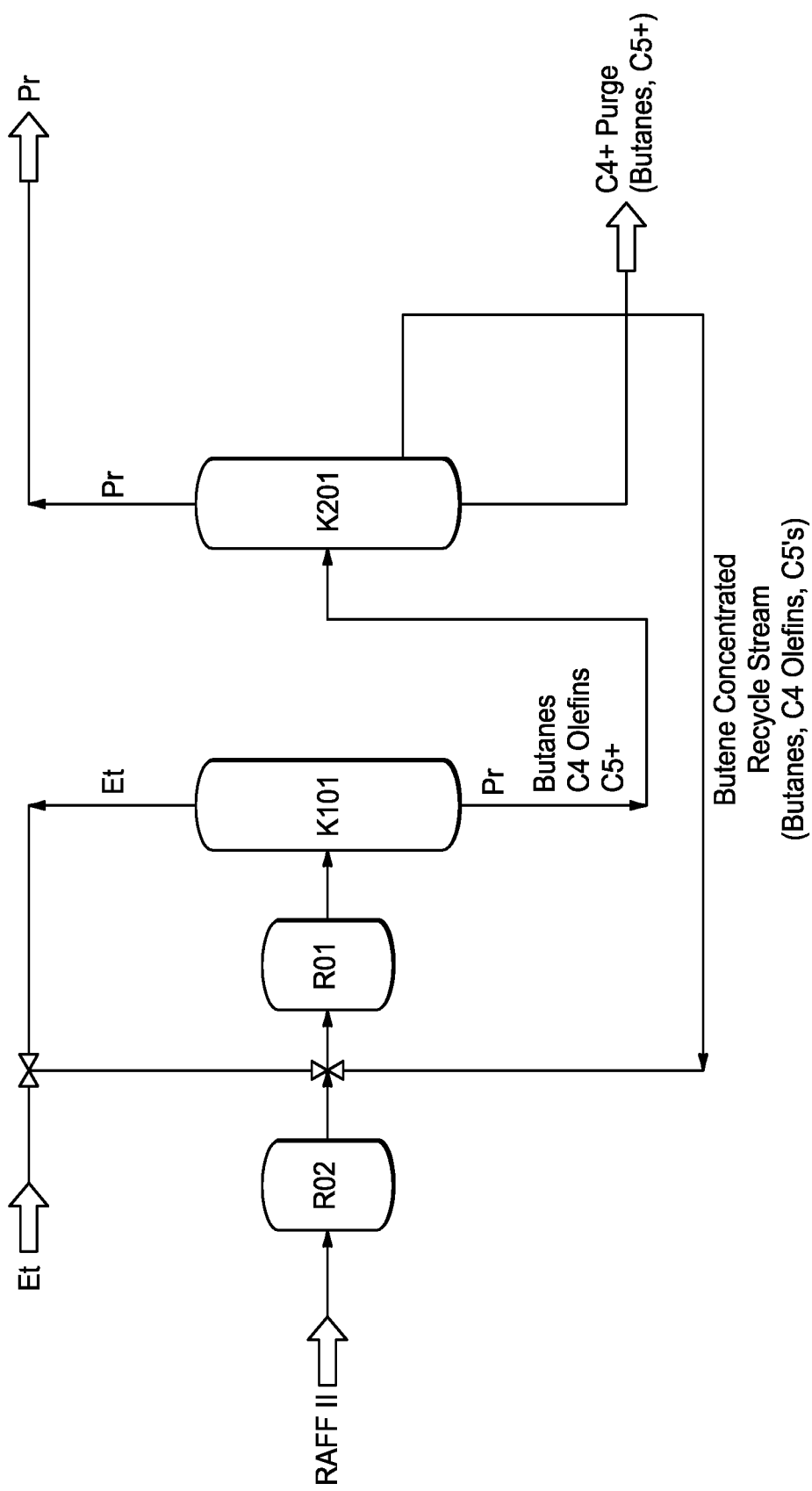
FIG. 3 is a schematic process flow diagram of a second embodiment in which a propylene product is produced utilizing a liquid isomerization reaction of a Raff II (i.e., fresh feed stream) prior to entering a metathesis reactor. Liquid isomerization reactor can be located either on fresh feed or on fresh feed plus ethylene feed stream. The pentene content of the butene concentrated stream is optimized to block 1-butene side reactions in the metathesis reactor.

FIG. 3 presents an embodiment utilizing an external liquid phase isomerization reactor (R02) in a Raffinate II feed stream, i.e., fresh feed stream, prior to entering a metathesis reactor (R01).

As in FIG. 2 the R02 reactor in FIG. 3 is operated under liquid phase conditions, which ensures the higher conversion of 1-butene- to 2-butene and thus provides for better selectivity, conversion, and ultimate yield of the overall metathesis process. As discussed above in FIG. 2 the metathesis reactor R01 of FIG. 3 provides a product stream comprising ethylene, propylene, $C_4$ olefins comprising 2-butene and 1-butene, heavier olefins, and paraffins wherein the product stream is processed in deethylenizer K-101 to separate ethylene, and a bottoms stream comprising propylene, butanes ($C_4$ paraffins), $C_4$ olefins, and $C_{5+}$ that is forwarded to depropylenizer K-201. The recovered ethylene from K-101 deethylenizer is recycled back to the R01 metathesis reactor. Depropylenizer K-201 separates propylene and a butene concentrated recycle side stream which is sent back to R-01 and a bottom cut. The butene concentrated recycle stream from depropylenizer K-201 contains some $C_4$ paraffins, most of $C_4$ olefins, and some $C_5$. The bottom cut of the depropylenizer K-201 ensures purging of $C_4$ paraffins that would otherwise buildup in the reactor recycle stream. It is thus rich in butanes but also contains butenes that are not easily separated from butanes, un-recycled $C_5$ and heavier products The external liquid phase isomerization reactor R02 can be located either on Raff II fresh feed or optionally on fresh feed plus ethylene feed stream (and/or the ethylene recycle stream). The lower temperature of the liquid phase isomerization reactor (R02) advantageously favors a higher ratio of 2-butene to 1-butene. After the fresh feed stream (i.e., Raff II) passes the external liquid phase isomerization reactor (R02) the isomerized stream is mixed with the butene concentrated recycled stream and with ethylene streams (both fresh and/or recycle ethylene unless those streams are already combined upstream R02) prior to entering the metathesis reactor (R01). The pentene content of the butene concentrated stream is optimized to block 1-butene side reactions in the metathesis reactor, for the reasons discussed above.

Figure 4:
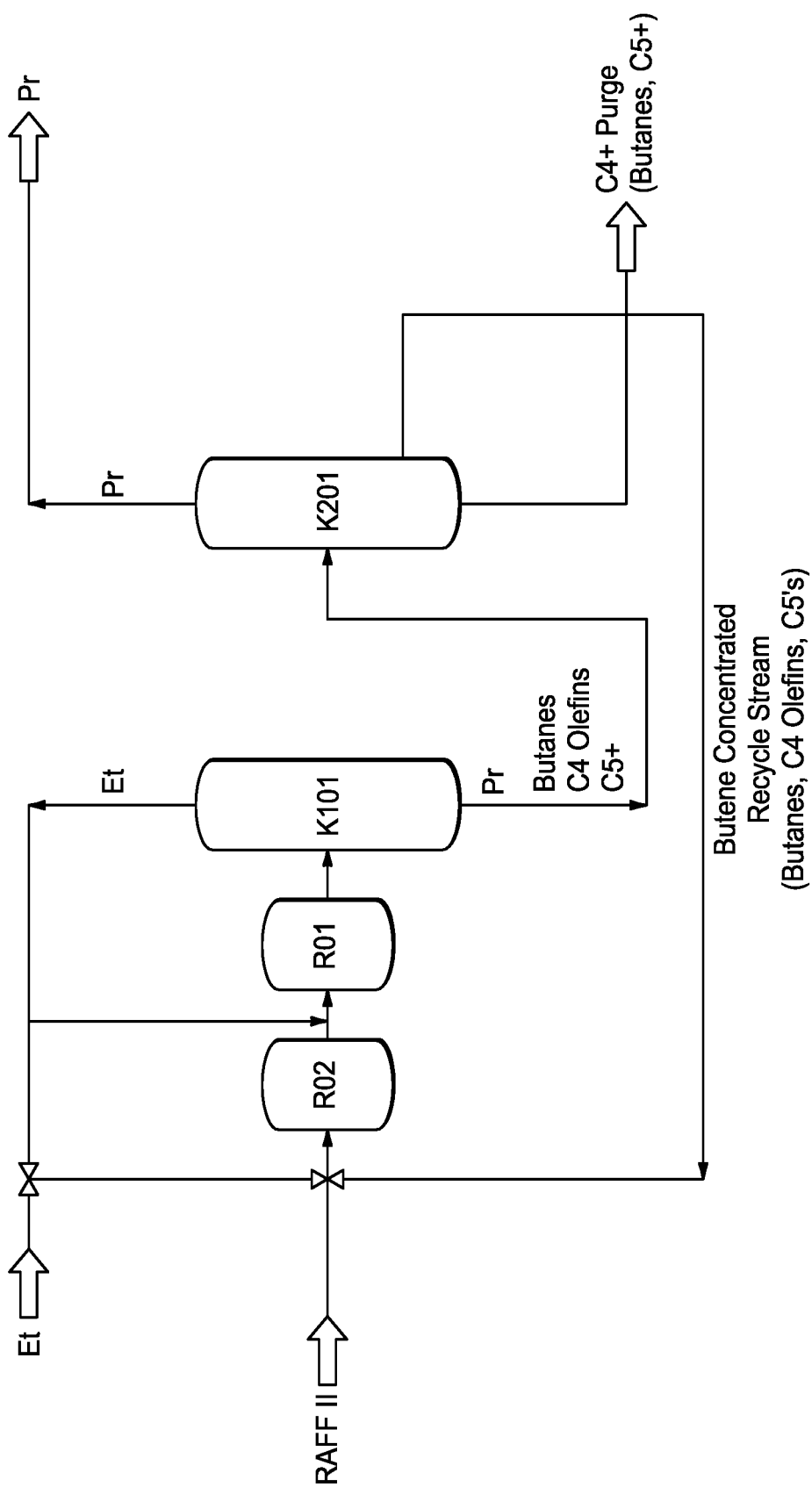
FIG. 4 is a process flow diagram of a third embodiment in which a propylene product is produced utilizing a liquid isomerization reaction of a Raff II (i.e., fresh feed) feed stream mixed with a butene concentrated recycle stream prior to entering a metathesis reactor. Ethylene feed stream can be either mixed before or after the liquid isomerization reactor. The pentene content of the butene concentrated stream is optimized to block 1-butene side reactions in the metathesis reactor.

FIG. 4 presents an embodiment utilizing an external liquid phase isomerization reactor (R02) upstream of the metathesis reactor (R01). In this embodiment Raff II (i.e., fresh feed) stream is mixed with the butene concentrated recycle stream prior to entering the external liquid phase isomerization reactor R02.

As in FIG. 2 and FIG. 3 the R02 reactor in FIG. 4 is operated under liquid phase conditions, which ensures the higher conversion of 1-butene- to 2-butene and thus provides for better selectivity, conversion, and ultimate yield of the overall metathesis process. As discussed above in FIG. 2 and FIG. 3 the metathesis reactor R01 of FIG. 4 provides a product stream comprising, ethylene, propylene, $C_4$ olefins comprising 2-butene and 1-butene, heavier olefins, and paraffins wherein the product stream is processed in deethylenizer K-101 to separate ethylene, and a bottoms stream comprising propylene, butanes (C$_4$ paraffins), C$_4$ olefins, and C$_{5+}$ that is forwarded to depropylenizer K-201. The recovered ethylene from K-101 deethylenizer is recycled back to the R01 metathesis reactor. Depropylenizer K-201 separates propylene and a butene concentrated recycle stream side stream which is sent back to R-01 and a bottom cut. The butene concentrated recycle stream from depropylenizer K-201 contains some C$_4$ paraffins, most of C$_4$ olefins, and some C$_5$. The bottom cut of the depropylenizer K-201 ensures purging of C$_4$ paraffins that would otherwise buildup in the reactor recycle stream. It is thus rich in butanes but also contains butenes that are not easily separated from butanes, un-recycled C$_5$ and heavier products.

The external liquid phase isomerization reactor R02 can be located either on combined Raff II (i.e., fresh feed) stream plus butene concentrated recycle stream or optionally on combined Raff II (i.e., fresh feed) stream plus butene concentrated recycle stream plus ethylene feed stream (and/or ethylene recycle stream). The lower temperature of the liquid phase isomerization reactor (R02) advantageously favors a higher ratio of 2-butene to 1-butene. The isomerized stream from the external liquid phase isomerization reactor (R02) is mixed with ethylene recycle stream (both fresh and recycle ethylene streams can be combined upstream R02) prior to entering the metathesis reactor (R01). The pentene content of the butene concentrated stream is optimized to block 1-butene side reactions in the metathesis reactor, for the reasons discussed above.

Figure 5:
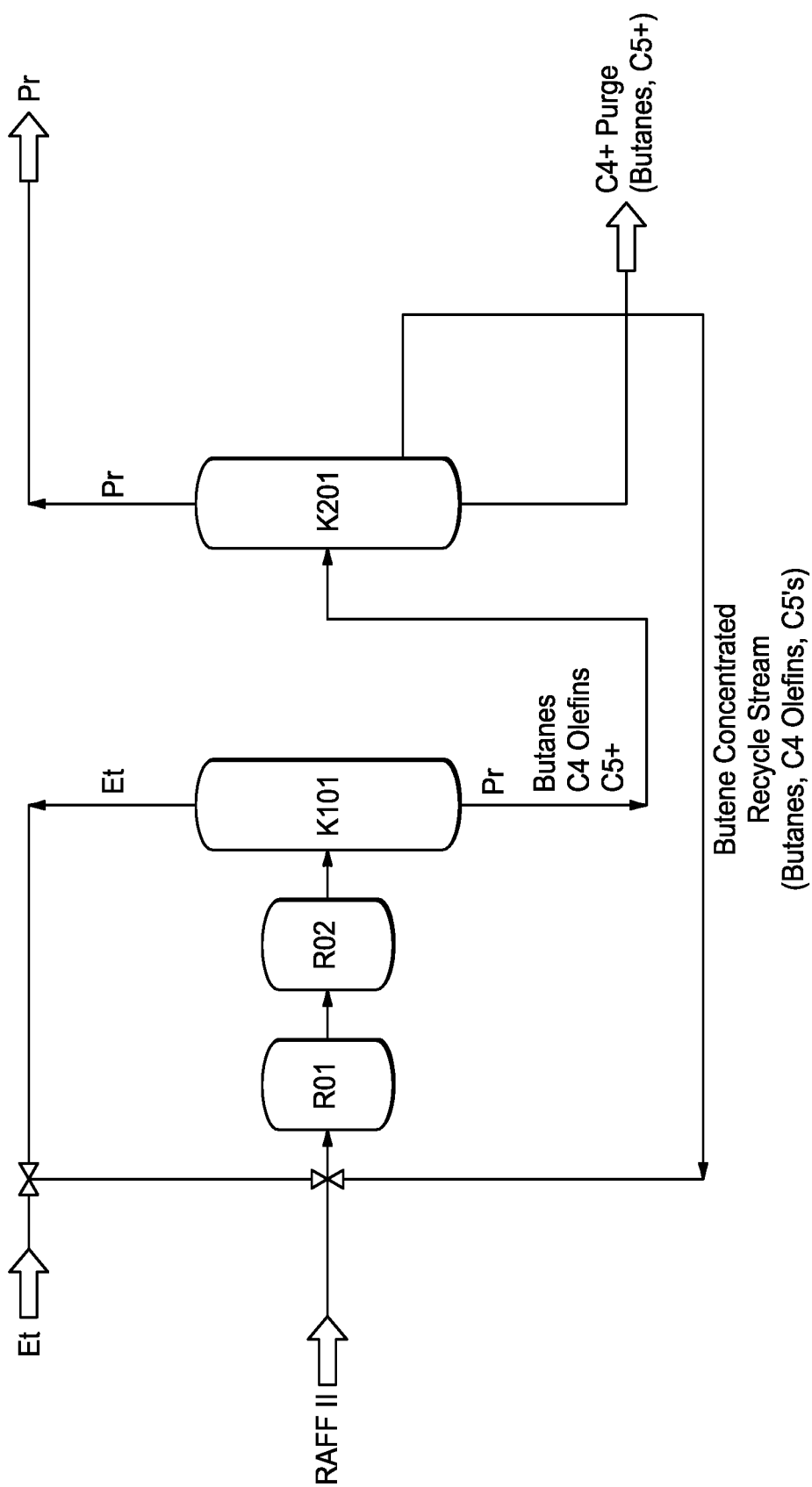
FIG. 5 is a process flow diagram of a fourth embodiment in which a propylene product is produced utilizing a liquid isomerization reaction of a metathesis reactor effluent that is produced from a Raff II (i.e., fresh feed) feed stream mixed with an ethylene feed stream and butene concentrated recycle stream prior to entering the metathesis reactor. The pentene content of the butene concentrated stream is optimized to block 1-butene side reactions in the metathesis reactor.

FIG. 5 presents an embodiment utilizing an external liquid phase isomerization reactor R02 downstream of the metathesis reactor R01. In this embodiment a Raff II (i.e., fresh feed) stream is mixed with the butene concentrated recycle steam, and an ethylene feed (and/or the ethylene recycle stream) prior to entering the metathesis reactor R01 to provide a product stream comprising ethylene, propylene, C$_4$ olefins comprising 2-butene and 1-butene, heavier olefins, and paraffins. The product stream is isomerized in the isomerization reactor R02 prior to the product stream being processed in deethylenizer K-101 to separate ethylene, and a bottoms stream comprising propylene, butanes (C$_4$ paraffins), C$_4$ olefins, and C$_{5+}$ that is forwarded to depropylenizer K-201. The recovered ethylene from K-101 deethylenizer is recycled back to the R01 metathesis reactor. Depropylenizer K-201 separates propylene and a butene concentrated recycle stream side stream which is sent back to R-01 and a bottom cut. The butene concentrated recycle stream from depropylenizer K-201 contains some C$_4$ paraffins, most of C$_4$ olefins, and some C$_5$. The bottom cut of the depropylenizer K-201 ensures purging of C$_4$ paraffins that would otherwise buildup in the reactor recycle stream. It is thus rich in butanes but also contains butenes that are not easily separated from butanes, un-recycled C$_5$ and heavier products.

In FIG. 5 like the embodiments of FIGS. 2-4 the lower temperature of the liquid phase isomerization reactor (R02) advantageously favors a higher ratio of 2-butene to 1-butene. The pentene content of the butene concentrated stream is optimized to block 1-butene side reactions in the metathesis reactor (refer the reasons discussed above).

It is contemplated herein that the use of special piping designed to accommodate the various locations of the external liquid phase isomerization reactor brings advantage. Such arrangement will allow to accommodate various feedstocks with compositions that change over the time, and provide for each feedstock the process configuration that maximize the propylene production. Indeed, depending on the type of heavy molecules processed in the steam cracking and also depending of the upstream units operation, such as butene-1 extraction unit, herein processes may have to process a wide range of feedstock composition, with ratio of butene-2 to butene-1 in the feedstock varying from 0.5 to 200.

It is contemplated herein that the addition of an external liquid phase isomerization reactor as described in the different figures can bring efficient debottlenecking solution to increase capacity of an existing metathesis unit.

Prophetic Examples

In order to provide a better understanding of the foregoing discussion, the following non-limiting prophetic examples are offered. Although the prophetic examples may be directed to specific embodiments, they are not to be viewed as limiting the invention in any specific respect.

Table 1: Feedstock examples include a Raffinate II (Raff-2), a Raffinate III (Raff-3), and two Raffinate mixtures (Raff mix) resulting from the mix of two Raffinate-II originating from one steam cracker unit and one FCC unit.

TABLE 1

| Component | Raff-2 mol % | Raff-3 mol % | Raff mix 1 mol % | Raff mix 2 mol % |
|---|---|---|---|---|
| Propylene | | | 0.7 | 0.7 |
| t,2-butene | 26.5 | 52.8 | 39.8 | 41.3 |
| c,2-butene | 13.3 | 26.7 | 19.8 | 20.3 |
| 1-butene | 51.2 | 0.6 | 5.3 | 3.1 |
| n-butane | 8.0 | 16.9 | 26.0 | 26.0 |
| i-butane | 0.0 | <1 | 5.4 | 5.4 |
| i-butene | 1.0 | 3.0 | 2.1 | 2.1 |
| C$_5$'s | | | 1.1 | 1.1 |
| Total | 100.0 | 100.0 | 100.0 | 100.0 |
| 2-butene/1-butene ratio | 0.8 | 136.1 | 11.2 | 19.9 |

The effect of isomerization on the raffinate feeds of Table 1 are as follows: For Raff-3 feed, which contains only 2-butene (cis and trans), there is no propylene production gain for adding an isomerization reactor on the recycle or anywhere else in the flowsheet. Indeed, the quantity of 1-butene anywhere in the process is so low that 1-butene to 2-butene isomerization reaction is either at equilibrium or in favor of converting 2-butene to 1-butene-1, leading to reduced propylene production.

For the Raff-2 stream of Table 1, which is rich in 1-butene, there is a significant propylene yield gain when a liquid phase isomerization reactor is used to isomerize the 1-butene to 2-butene from the butene concentrated recycle stream. For Raff-2 stream, higher propylene production can also be achieved with an external liquid phase isomerization reactor on the fresh feedstock (FIG. 3 flow scheme) and in lieu of an isomerization reactor placed on the butene concentrated recycle stream (FIG. 2 flow scheme).

The mixed raffinate feeds (raff mix 1 and raff mix 2) have less 1-butene than the Raff-2 feed but more than Raff-3. Thus, for this type of feed, propylene production is slightly increased by introducing an external liquid isomerization reactor in the scheme. Propylene gain is proportional to the amount of 1-butene in the fresh feed. The efficiency of the external liquid phase isomerization reactor on the butene concentrated recycle stream (FIG. 2 flow scheme) compared to location on fresh feedstock (FIG. 3 flow scheme) depends on the 2-butene/1-butene ratio and optimum location shall be determined by a case by case study. As an illustration, Table 2 provides a comparison of the key performances of a metathesis process for various location of isomerization reactor in the process flow scheme.

TABLE 2: Impact of Isomerization Reactor location in the Metathesis Flow scheme for the Various Feedstocks of Table 1

TABLE 2

| | | Conventional Scheme (FIG. 1) | Conventional Scheme (FIG. 1) | External Liquid Isomerization (FIG. 3) | External Liquid Isomerization (FIG. 2) |
|---|---|---|---|---|---|
| Isomerization Reactor Details | Isomerization function | No | Yes | Yes | Yes |
| | Isomerization catalyst location | — | Metathesis Reactor | Fresh Feed | Recycle Stream |
| | Operating Conditions | — | Vapor Phase, 300° C. | Liquid Phase, 100° C. | Liquid Phase, 100° C. |
| Raff-3 2-butene only B2/B1 = 136.1 | B2/B1 Isomerization inlet | / | 10 | 136 | 21 |
| | B2/B1 Isomerization outlet | / | 5.5 | 19 | 19 |
| | Butene Conversion | 71.5% | 66.6% | 68.9% | 71.5% |
| | Butene Selectivity | 99.3% | 94.9% | 96.9% | 99.2% |
| | Ultimate propylene yield | 90.9% | 83.4% | 86.8% | 90.8% |
| Raff-2 1-butene rich B2/B1 = 0.8 | B2/B1 Isomerization inlet | / | 1 | 0.8 | 0.4 |
| | B2/B1 Isomerization outlet | / | 5.5 | 19 | 19 |
| | Butene Conversion | 37.0% | 66.7% | 68.1% | 56.7% |
| | Butene Selectivity | 64.2% | 95.1% | 96.3% | 86.1% |
| | Ultimate propylene yield | 40.3% | 87.3% | 89.3% | 73.1% |
| Raff Mix1 Moderate 1-butene B2/B1 = 11.2 | B2/B1 Isomerization inlet | / | 5.9 | 11.2 | 4.2 |
| | B2/B1 Isomerization outlet | / | 5.5 | 19.0 | 19 |
| | Butene Conversion | 66.3% | 65.7% | 67.9% | 68.5% |
| | Butene Selectivity | 97.1% | 96.6% | 98.7% | 99.1% |
| | Ultimate propylene yield | 83.1% | 82.1% | 85.9% | 86.7% |
| Raff Mix2 Moderate 1-butene B2/B1 = 19.9 | B2/B1 Isomerization inlet | / | 7.8 | 19.9 | 7.5 |
| | B2/B1 Isomerization outlet | / | 5.5 | 19.0 | 19 |
| | Butene Conversion | 70.0% | 66.7% | 69.3% | 70.3% |
| | Butene Selectivity | 97.6% | 95.0% | 97.4% | 98.4% |
| | Ultimate propylene yield | 85.9% | 81.1% | 85.4% | 87.1% |

In order to characterize the performances of the overall metathesis scheme, three key parameters are compared:

Butene Conversion $$\text{Butene conversion} = \frac{(\text{butene}-1+\text{butene}-2)_{reactor\,inlet} - (\text{butene}-1+\text{butene}-2)_{reactor\,outlet}}{(\text{butene}-1+\text{butene}-2)_{reactor\,inlet}}$$

Reactor Shall be Understood as Metathesis Reactor

Butene Selectivity $$\text{Selectivity} = \frac{\text{Propylene produced}/2}{(\text{butene}-1+\text{butene}-2)\,\text{reacted}} \text{ in mol}$$

Propylene Ultimate Yield $$\text{Ultimate yield} = \frac{\text{Propylene produced}/2}{(\text{Butene}-1+\text{Butene}-2)_{C4\,Cut\,Fresh\,Feed}} \text{ in mol}$$

First conclusion of Table 2 is that isomerization functionality must be added somewhere in the flowsheet for those feedstock with significant 1-butene content in the $C_4$ Raffinate feedstock to keep attractive performances (i.e., high butene conversion and selectivity and high propylene ultimate yield). There are several options for adding isomerization functionality among with: (a) Isomerize the 1-butene in the metathesis reactor (conventional flow scheme, FIG. 1); (b) Isomerize the 1-butene in the fresh feed (FIG. 3); (c) Isomerize the 1-butene in the butene concentrated recycle stream (FIG. 2); (d) Isomerize the 1-butene in the mixed fresh feed that is mixed with the butene concentrated recycle stream to the metathesis reactor (FIG. 4); and (e) Isomerize the 1-butene in the metathesis reactor effluent (FIG. 5). Definition of optimum location depends on fresh feed composition and is discussed here-below.

According to an embodiment isomerization in an external liquid phase isomerization reactor is effective for increasing propylene production from feedstocks rich in 1-butene (i.e., Raff-2) in comparison to isomerization in the reactor as per conventional scheme. In this regard, more 1-butene is isomerized to 2-butenes, which is then available for the main metathesis reaction resulting in increased propylene yield. This statement is highlighted by Table 2. Ultimate yield of propylene of the unit in case a liquid isomerization reactor is installed on the fresh feed is increased by about 2.3% compared to a vapor isomerization in the metathesis reactor. However, one should notice that for these feedstocks rich in 1-butene (i.e. Raff-2 or more generally feedstocks with B2/B1 ratio below about 10) external liquid isomerization located on fresh feed is more effective compared to location on butene concentrated recycle stream. Indeed, in the example provided in Table 2, for Raff-2 feedstock, propylene ultimate yield is about 89% for liquid isomerization on fresh feed while it is 73% for liquid isomerization on butene concentrated recycle stream.

From Table 2, for moderate 1-butene content in the fresh feed, having isomerization in the butene concentrated recycle stream increases the ultimate yield of propylene of the unit compared to isomerization in the metathesis reactor. Indeed, at a 2-butene to 1-butene ratio of 11.2 (i.e., Raff mix 1) and 19.9 (i.e., Raff mix 2) the ultimate yield of propylene is increase by respectively approximately 6% and 7%. For these feedstock having Butene2/Butene1 ratio between about 10 and 20 it is more attractive to locate external liquid isomerization on recycle stream than on fresh feed.

The data from Table 2 indicates that adding an isomerization functionality in the metathesis scheme induces a negative impact on propylene production if fresh feed is butene-2 rich (i.e., Raff-3). Indeed ultimate yield of propylene is decreased by more than 8% when a vapor phase isomerizer is added to the metathesis reactor compared to a metathesis catalyst only. However in case a liquid isomerization reactor is used impact is mitigated compared to a vapor isomerization reactor.

It can be taken from the data from Table 2 that conventional scheme with isomerization functionality in metathesis reactor induces a negative impact on propylene production if B2/B1 ratio of fresh feed is greater than the B2/B1 ratio at vapor isomerization reactor outlet. For these fresh feedstock having Butene2/Butene1 ratio higher than the one achievable at equilibrium at metathesis reactor condition, external liquid phase isomerizer is still attractive to overall Flow scheme (higher propylene ultimate yield achieved than conventional scheme without isomerization functionality).

According to another embodiment the use of elevated levels of 2-pentene in the butene concentrated recycle stream prevents 1-butene from consuming 2-butene or propylene in the metathesis reactor via side reactions, which ultimately leaves more 2-butene available for the main metathesis reactions, i.e., 2-butene plus ethylene to yield only propylene.

The effectiveness of 2-pentene reducing or stopping the reaction of 1-butene with propylene (i.e., 1-butene+propylene F←→ethylene+2-pentene) or the reaction of 1-butene with 2-Butene (i.e., 1-butene+2-butene←→propylene+2-pentene) depends on the relative quantity of 1-butene, 2-butene, propylene and 2-pentene in the metathesis reactor, which is highly dependent on fresh feed composition and of butene concentrated recycled stream composition. 2-pentene content at inlet of metathesis reactor can be adjusted based on 2-pentene content in the butene concentrated recycled stream. Optimization of 2-pentene content in the butene concentrated recycled stream is done per adjustment of the depropylenizer column K-201 operating parameters such as reflux flow, reboiling rate and side-draw location which set 2-pentene recovery achieved on this distillation column. Optimization of 2-pentene content in the butene concentrated recycled stream is thus a case by case study that should assess propylene production gain versus operability issues of the column. As an illustration, Table 3 provides a comparison of the ultimate yield of propylene for an increased recovery of 2-pentene in the depropylenizer column, leading to an increased concentration of 2-pentene in the recycle. 2-pentene recovery in the depropylenizer column (K-201) is calculated as 2-pentene in the side-draw from depropylenizer K-201, i.e. in the butene concentrated recycled stream divided by the 2-pentene feeding the column K-201. Table 3 is drawn for the mixed Raffinate feedstock (Raf Mix-1).

TABLE 3

| 2-Pentene recovery in K-201 | 2-Pentene concentration in butene concentrated recycle stream | Butene Conversion | Butene Selectivity | Ultimate Propylene Yield |
|---|---|---|---|---|
| 30% | 1.0% | 67.5% | 94.9% | 82.4% |
| 40% | 1.4% | 67.2% | 95.7% | 82.7% |
| 50% | 1.8% | 66.7% | 96.4% | 82.9% |
| 60% | 2.2% | 66.3% | 97.1% | 83.1% |
| 70% | 2.7% | 65.8% | 97.9% | 83.3% |
| 80% | 3.3% | 65.1% | 98.8% | 83.4% |
| 90% | 4.0% | 64.2% | 100.2% | 83.6% |

From Table 3, it is clear that ultimate propylene yield increases when 2-Pentene Recovery in K-201 increases. However, the gain is not linear and becomes marginal at high recovery rates. The optimization is a case by case study depending of the fresh feed composition and is a trade-off between propylene yields and potential induced operability issues such as difficult depropylenizer column bottom flow control if nearly no flow is purged, or lower run-length and/or lifetime of the metathesis catalyst if heavies are recycled.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims

What is claimed is:

1. A method for the production of propylene from ethylene and butene comprising:
   (i) isomerizing under liquid phase conditions a hydrocarbon stream in an isomerization reactor vessel, thereby producing an isomerized hydrocarbon stream;
   (ii) providing a feedstock comprising the isomerized hydrocarbon stream to a metathesis reactor vessel without distilling the isomerized hydrocarbon stream before the metathesis reactor vessel; and
   (iii) contacting the feedstock comprising the isomerized hydrocarbon stream with a metathesis catalyst in the metathesis reactor vessel to form a product stream,
   wherein (1) the isomerization reactor vessel that converts a portion of 1-butene to 2-butene is located on a butene concentrated recycle stream for making the feedstock to the metathesis reactor vessel comprising a Raffinate mixture, ethylene and the isomerized hydrocarbon stream, the Raffinate mixture having 2-butene/1-butene mole ratio between 10 and 20, or (2) the isomerization reactor vessel that converts a portion of 1-butene to 2-butene is located on a fresh feed stream for making the feedstock to the metathesis reactor vessel comprising a Raffinate mixture, ethylene and the isomerized hydrocarbon stream, the Raffinate mixture having 2-butene/1-butene mole ratio less than 10,
   wherein the hydrocarbon stream comprises n-butenes and paraffins in which butadiene is limited to a maximum of about 0.5 weight percent and isobutylene is limited to maximum of about 10 weight percent, and
   wherein the isomerization reactor vessel is external and separate from the metathesis reactor vessel.

2. The process of claim 1, wherein the product stream comprises ethylene, propylene, $C_4$ olefins comprising 2-butene and 1-butene, heavier olefins, and paraffins.

3. The process of claim 2, wherein ethylene is separated from the product stream to provide a recycle ethylene stream and a bottoms stream comprising propylene, paraffins, $C_4$ olefins comprising 2-butene to 1-butene, and $C_{5+}$ hydrocarbons.

4. The process of claim 3, wherein the bottoms stream is fractionated to provide at least (i) a propylene fraction, (ii) a butene concentrated recycle stream fraction comprising paraffins, olefins, 2-butene, 1-butene, and $C_5$ hydrocarbons, and (iii) a $C_{4+}$ hydrocarbon fraction.

5. The process of claim 4, wherein at least one of the recycle ethylene stream and the butene concentrated recycle stream fraction is recycled to and combined with the hydrocarbon stream.

6. The process of claim 5, wherein the butene concentrated recycle stream fraction is isomerized under liquid phase conditions in the isomerization reactor vessel.

7. The process of claim 1, wherein the liquid phase conditions include an amount of hydrogen.

8. A process for the production of propylene from ethylene and butene, the process comprising:
   (i) combining a hydrocarbon stream comprising n-butenes and paraffins in which butadiene is limited to a maximum of about 0.5 weight percent and isobutylene is limited to maximum of about 10 weight percent with an ethylene stream, thereby producing a combined hydrocarbon stream and ethylene stream;
   (ii) contacting a feedstock to the metathesis reactor vessel in a metathesis reactor vessel with a metathesis catalyst to form a product stream comprising ethylene, propylene, $C_4$ olefins comprising 2-butene and 1-butene, heavier olefins, and paraffins;
   (iii) separating the ethylene from the product stream to provide a recycle ethylene stream and a bottoms stream comprising propylene, paraffins, $C_4$ olefins comprising 2-butene and 1-butene, and $C_{5+}$ hydrocarbons;
   (iv) fractionating the bottoms stream to provide at least (1) a propylene fraction, (2) a butene concentrated recycle stream fraction comprising paraffins, olefins, 2-butene, 1-butene, and $C_5$ hydrocarbons, and (3) a $C_{4+}$ hydrocarbon fraction;
   (v) recycling the recycle ethylene stream of step (iii) and the butene concentrated recycle stream fraction of step (iv) to step (i), thereby making a feedstock to a liquid phase isomerization reactor vessel comprising the combined hydrocarbon stream and ethylene stream of step (i), the recycle ethylene stream of step (iii), the butene concentrated recycle stream fraction of step (iv), and a Raffinate mixture having 2-butene/1-butene mole ratio less than 10; and
   (vi) isomerizing the feedstock to the liquid phase isomerization reactor vessel under liquid phase conditions in the liquid phase isomerization reactor vessel, thereby producing an isomerized hydrocarbon stream, the isomerized hydrocarbon stream is transported to the metathesis reactor vessel without distilling the isomerized hydrocarbon stream before the metathesis reactor vessel, the feedstock to the metathesis reactor vessel comprises the isomerized hydrocarbon stream,
   wherein the liquid phase isomerization reactor vessel is external and separate from the metathesis reactor vessel.

9. The process of claim 8, wherein the ethylene stream and/or the recycle ethylene stream are combined with the hydrocarbon stream or with a combination stream comprising the butene concentrated recycle stream fraction and the hydrocarbon stream prior to the isomerizing step (vi).

10. The process of claim 8, wherein 2-pentene content of the butene concentrated recycle stream fraction is adjusted based on a composition of the combined hydrocarbon stream and ethylene stream of step (i) by means of 2-pentene recovery optimization of the fractionating step (iv).

11. The process of claim 10, wherein as the 2-pentene content of the butene concentrated recycle stream fraction increases, the amount of propylene produced by the process increases.

12. The process of claim 8, wherein the liquid phase isomerization reactor vessel converts a portion of 1-butene to 2-butene.

13. The process of claim 8, wherein the liquid phase conditions include an amount of hydrogen.

14. The process of claim 8, wherein the hydrocarbon stream is a $C_4$ feedstock from of a steam cracking and/or from refinery FCC unit, and/or a $C_4$ raffinate.

15. A process for the production of propylene from ethylene and butene, the process comprising:
   (i) combining a hydrocarbon stream comprising n-butenes and paraffins in which butadiene is limited to a maximum of about 0.5 weight percent and isobutylene is limited to maximum of about 10 weight percent with an ethylene stream, thereby producing a combined hydrocarbon stream and ethylene stream;
   (ii) contacting a feedstock to the metathesis reactor vessel in a metathesis reactor vessel with a metathesis catalyst to form a product stream comprising ethylene, propylene, $C_4$ olefins comprising 2-butene and 1-butene, heavier olefins, and paraffins;
   (iii) separating the ethylene from the product stream to provide a recycle ethylene stream and a bottoms stream comprising propylene, paraffins, $C_4$ olefins comprising 2-butene and 1-butene, and $C_{5+}$ hydrocarbons;

(iv) fractionating the bottoms stream to provide at least (1) a propylene fraction, (2) a butene concentrated recycle stream fraction comprising paraffins, olefins, 2-butene, 1-butene, and $C_5$ hydrocarbons, and (3) a $C_{4+}$ hydrocarbon fraction;

(v) recycling the recycle ethylene stream of step (iii) to step (i), thereby making the feedstock to the metathesis reactor vessel comprising the combined hydrocarbon stream and ethylene stream of step (i), the recycle ethylene stream of step (iii), and a Raffinate mixture having 2-butene/1-butene mole ratio between 10 and 20; and (vi) isomerizing under liquid phase conditions in a liquid phase isomerization reactor vessel the butene concentrated recycle stream fraction prior to step (i), wherein the liquid phase isomerization reactor vessel is located on a butene concentrated recycle stream for producing an isomerized hydrocarbon stream to be combined with the feedstock to the metathesis reactor vessel and to be provided to the metathesis reactor vessel, and wherein the liquid phase isomerization reactor vessel is external and separate from the metathesis reactor vessel.

16. The process of claim 15, wherein the ethylene stream and/or the recycle ethylene stream are combined with the hydrocarbon stream prior to the isomerizing step (vi).

17. The process of claim 15, wherein 2-pentene content of the butene concentrated recycle stream fraction is adjusted based on a composition of the combined hydrocarbon stream and ethylene stream of step (i) by means of 2-pentene recovery optimization of the fractionating step (iv).

18. The process of claim 17, wherein as the 2-pentene content of the butene concentrated recycle stream fraction increases, the amount of propylene produced by the process increases.

19. The process of claim 15, wherein the liquid phase isomerization reactor vessel converts a portion of 1-butene to 2-butene.

20. The process of claim 15, wherein the liquid phase conditions include an amount of hydrogen.

21. The process of claim 15, wherein the hydrocarbon stream is a $C_4$ feedstock from of a steam cracking and/or from refinery FCC unit, and/or a $C_4$ raffinate.

* * * * *